US011414517B2

(12) United States Patent
Choi et al.

(10) Patent No.: US 11,414,517 B2
(45) Date of Patent: Aug. 16, 2022

(54) LOW-TEMPERATURE PROCESSABLE ALIPHATIC POLYESTER

(71) Applicant: CJ CHEILJEDANG CORPORATION, Seoul (KR)

(72) Inventors: Jin Woo Choi, Seoul (KR); Yunjae Jang, Seoul (KR); Soyun Park, Seoul (KR); Dong-eun Chang, Woburn, MA (US); John Licata, Woburn, MA (US)

(73) Assignee: CJ CHEILJEDANG CORPORATION, Seoul (KR)

( * ) Notice: Subject to any disclaimer, the term of this patent is extended or adjusted under 35 U.S.C. 154(b) by 234 days.

(21) Appl. No.: 16/854,070

(22) Filed: Apr. 21, 2020

(65) Prior Publication Data

US 2021/0324136 A1    Oct. 21, 2021

(51) Int. Cl.
| | |
|---|---|
| *C08L 67/02* | (2006.01) |
| *C08G 63/06* | (2006.01) |
| *C12P 19/32* | (2006.01) |

(52) U.S. Cl.
CPC .............. *C08G 63/06* (2013.01); *C12P 19/32* (2013.01)

(58) Field of Classification Search
USPC ........................................ 528/271, 272, 361
See application file for complete search history.

(56) References Cited

U.S. PATENT DOCUMENTS 8,383,379 B2   2/2013  Park et al.

FOREIGN PATENT DOCUMENTS

| WO | 2014-028943 A1 | 2/2014 |
| WO | 2014-058655 A1 | 4/2014 |

OTHER PUBLICATIONS

Henry E. Valentin et al.; Metabolic pathway for biosynthesis of poly(3-hydroxybutyrate-co-4-hydroxybutyrate); Eur. J. Biochem. 227, 43-60 (1995) (Year: 1995).*
Norhafini et al., "Synthesis of poly(3-hydroxybutyrate-co-4-hydroxybutyrate) with high 4HB composition and PHA content using 1,4-butanediol and 1,6-hexanediol for medical application", Journal of Polymer Research, vol. 24 No. 189, (2017).
Nakamura et al., "Microbial Synthesis and Characterization of Poly(3-hydroxybutyrate-co-4-hydroxybutyrate)", American Chemical Society, vol. 25 No. 17, p. 4237-4241, (Aug. 17, 1992).
International Search Report for Application No. PCT/KR2021/003923 dated Jul. 21, 2021.

* cited by examiner

*Primary Examiner* — Terressa Boykin
(74) *Attorney, Agent, or Firm* — Christensen, Fonder, Dardi & Herbert PLLC; Diane E. Bennett; Peter S. Dardi

(57) ABSTRACT

A low-temperature processable aliphatic polyester having 3-hydroxybutyrates (3HB) and 4-hydroxybutyrates (4-HB) as basic repeated structures and an adjusted content of 4-hydroxybutyrates (4HB) is described. Articles based on the aliphatic polyesters are described and include a biodegradable wax, a medical device, a low-temperature hot melt, a non-woven cloth, a bioplastic, a drug carrier, a medical wrap, a medical fiber, a medical filament, a medical stent, or an orthopedic prosthesis. Methods for preparing the aliphatic polyesters are described.

21 Claims, 3 Drawing Sheets

Specification includes a Sequence Listing.

SEQUENCE LISTING

<160> NUMBER OF SEQ ID NOS: 6

<210> SEQ ID NO 1
<211> LENGTH: 1362
<212> TYPE: DNA
<213> ORGANISM: Clostridium kluyveri

<400> SEQUENCE: 1

```
atgtccaacg aggttagcat taaggagctg attgagaagg cgaaagtggc gcagaaaaag      60
ctggaagcgt atagccaaga gcaagttgac gttctggtca aggcgctggg taaagttgtg     120
tacgacaacg ccgagatgtt gcgaaagagg cggtggagga aaccgagatg ggtgtttacg     180
aggataaagt ggctaaatgt catctgaaat ctggtgcaat ctggaatcac attaaagata     240
agaaaaccgt tggtattatc aaggaagaac cggagcgtgc gctggtgtac gtcgcgaagc     300 ctaaggtgt tgtggcggcg acgaccccta tcaccaatcc tgtggttacc ccgatgtgta     360
acgcgatggc agcaattaaa ggtcgcaaca ccatcattgt cgccccgca tccgaaggcg     420 aagaaggtga gcgcgcacac cgtggagctg atgaatgcag aactgaaaaa gttgggtgcg     480
ccggaaaaca ttatccagat cgttgaagcc ccaagccgtg aagcagccaa ggagttgatg     540
gagagcgcag acgtggttat cgccacgggt ggcgcaggc gtgttaaagc agcgtactcc     600
tccggccgtc cggcatacgg tgtcggtccg ggcaattctc aggtcattgt cgataagggt     660
```

```
tacgattata caaaagctgc ccaggacatc attaccggcc gcaagtatga caacggtatc    720
atttgcagct ctgagcagag cgtgatcgca ccggcggagg actacgacaa ggtcatcgcg    780
gctttcgtcg agaatggcgc gttctatgtc gaggatgagg aaactgtgga gaaattccgt    840
agcacgctgt tcaaggatgg caagatcaat agcaaaatca tcggtaaatc cgtgcagatc    900
atcgctgacc tggctggtgt caaggtgccg gaaggcacca aggtgatcgt gttgaagggc    960
aagggtgccg gtgaaaagga cgttctgtgc aaggagaaaa tgtgcccggt cctggttgcc   1020
ctgaaatatg acacctttga ggaggcggtc gagatcgcga tggccaacta tatgtacgag   1080
ggtgcgggcc ataccgccgg tatccacagc gataacgacg agaatatccg ctacgcgggt   1140
acggtgctgc caatcagccg tctggttgtc aaccagccag caactacggc cggtggtagc   1200
tttaacaatg gttttaatcc gaccaccacc ttgggctgcg gtagctgggg ccgtaactcc   1260
attagcgaga acctgacgta tgagcatctg attaatgtca gccgtattgg ctatttcaat   1320
aaggaggcaa agttcctag ctacgaggag atctggggtt aa                       1362
```

<210> SEQ ID NO 2
<211> LENGTH: 453
<212> TYPE: PRT
<213> ORGANISM: Clostridium kluyveri

<400> SEQUENCE: 2

```
Met Ser Asn Glu Val Ser Ile Lys Glu Leu Ile Glu Lys Ala Lys Val
1               5                   10                  15

Ala Gln Lys Lys Leu Glu Ala Tyr Ser Gln Glu Gln Val Asp Val Leu
            20                  25                  30

Val Lys Ala Leu Gly Lys Val Val Tyr Asp Asn Ala Glu Met Phe Ala
        35                  40                  45

Lys Glu Ala Val Glu Glu Thr Glu Met Gly Val Tyr Glu Asp Lys Val
    50                  55                  60

Ala Lys Cys His Leu Lys Ser Gly Ala Ile Trp Asn His Ile Lys Asp
65                  70                  75                  80

Lys Lys Thr Val Gly Ile Ile Lys Glu Glu Pro Glu Arg Ala Leu Val
                85                  90                  95

Tyr Val Ala Lys Pro Lys Gly Val Val Ala Ala Thr Thr Pro Ile Thr
            100                 105                 110

Asn Pro Val Val Thr Pro Met Cys Asn Ala Met Ala Ala Ile Lys Gly
        115                 120                 125

Arg Asn Thr Ile Ile Val Ala Pro His Pro Lys Ala Lys Lys Val Ser
    130                 135                 140

Ala His Thr Val Glu Leu Met Asn Ala Glu Leu Lys Lys Leu Gly Ala
145                 150                 155                 160

Pro Glu Asn Ile Ile Gln Ile Val Glu Ala Pro Ser Arg Glu Ala Ala
                165                 170                 175

Lys Glu Leu Met Glu Ser Ala Asp Val Val Ile Ala Thr Gly Gly Ala
            180                 185                 190

Gly Arg Val Lys Ala Ala Tyr Ser Ser Gly Arg Pro Ala Tyr Gly Val
        195                 200                 205

Gly Pro Gly Asn Ser Gln Val Ile Val Asp Lys Gly Tyr Asp Tyr Asn
    210                 215                 220

Lys Ala Ala Gln Asp Ile Ile Thr Gly Arg Lys Tyr Asp Asn Gly Ile
225                 230                 235                 240

Ile Cys Ser Ser Glu Gln Ser Val Ile Ala Pro Ala Glu Asp Tyr Asp
                245                 250                 255
```

Lys Val Ile Ala Ala Phe Val Glu Asn Gly Ala Phe Tyr Val Glu Asp
            260                 265                 270

Glu Glu Thr Val Glu Lys Phe Arg Ser Thr Leu Phe Lys Asp Gly Lys
        275                 280                 285

Ile Asn Ser Lys Ile Ile Gly Lys Ser Val Gln Ile Ile Ala Asp Leu
    290                 295                 300

Ala Gly Val Lys Val Pro Glu Gly Thr Lys Val Ile Val Leu Lys Gly
305                 310                 315                 320

Lys Gly Ala Gly Glu Lys Asp Val Leu Cys Lys Glu Lys Met Cys Pro
                325                 330                 335

Val Leu Val Ala Leu Lys Tyr Asp Thr Phe Glu Glu Ala Val Glu Ile
            340                 345                 350

Ala Met Ala Asn Tyr Met Tyr Glu Gly Ala Gly His Thr Ala Gly Ile
        355                 360                 365

His Ser Asp Asn Asp Glu Asn Ile Arg Tyr Ala Gly Thr Val Leu Pro
    370                 375                 380

Ile Ser Arg Leu Val Val Asn Gln Pro Ala Thr Thr Ala Gly Gly Ser
385                 390                 395                 400

Phe Asn Asn Gly Phe Asn Pro Thr Thr Thr Leu Gly Cys Gly Ser Trp
                405                 410                 415

Gly Arg Asn Ser Ile Ser Glu Asn Leu Thr Tyr Glu His Leu Ile Asn
            420                 425                 430

Val Ser Arg Ile Gly Tyr Phe Asn Lys Glu Ala Lys Val Pro Ser Tyr
        435                 440                 445

Glu Glu Ile Trp Gly
    450

<210> SEQ ID NO 3
<211> LENGTH: 870
<212> TYPE: DNA
<213> ORGANISM: Arabidopsis thaliana

<400> SEQUENCE: 3
atggaagtag gttttctggg tctgggcatt atgggtaaag ctatgtccat gaacctgctg      60
aaaaacggtt tcaaagttac cgtgtggaac cgcactctgt ctaaatgtga tgaactggtt     120
gaacacggtg caagcgtgtg cgagtctccg gctgaggtga tcaagaaatg caaatacacg     180
atcgcgatgc tgagcgatcc gtgtgcagct ctgtctgttg ttttcgataa aggcggtgtt     240
ctggaacaga tctgcgaggg taagggctac atcgacatgt ctaccgtcga cgcggaaact     300
agcctgaaaa ttaacgaagc gatcacgggc aaaggtggcc gttttgtaga aggtcctgtt     360
agcggttcca aaaagccggc agaagacggc cagctgatca tcctggcagc aggcgacaaa     420
gcactgttcg aggaatccat cccggccttt gatgtactgg caaacgttc cttttatctg      480 ggtcaggtgg gtaacggtgc gaaaatgaaa ctgattgtta acatgatcat gggttctatg     540
atgaacgcgt ttagcgaagg tctggtactg gcagataaaa gcggtctgtc tagcgacacg     600
ctgctggata ttctggatct gggtgctatg acgaatccga tgttcaaagg caaggtccg      660 tccatgacta aatccagcta cccaccggct ttcccgctga acaccagca gaaagacatg      720 cgtctggctc tggctctggg cgacgaaaac gctgttagca tgccggtcgc tgcggctgcg    780
aacgaagcct tcaagaaagc ccgtagcctg ggcctgggcg atctggactt ttctgctgtt    840
atcgaagcgg taaaattctc tcgtgaataa                                      870

<210> SEQ ID NO 4
<211> LENGTH: 289
<212> TYPE: PRT
<213> ORGANISM: Arabidopsis thaliana

<400> SEQUENCE: 4

```
Met Glu Val Gly Phe Leu Gly Leu Gly Ile Met Gly Lys Ala Met Ser
 1               5                  10                  15

Met Asn Leu Leu Lys Asn Gly Phe Lys Val Thr Val Trp Asn Arg Thr
            20                  25                  30

Leu Ser Lys Cys Asp Glu Leu Val Glu His Gly Ala Ser Val Cys Glu
        35                  40                  45

Ser Pro Ala Glu Val Ile Lys Lys Cys Lys Tyr Thr Ile Ala Met Leu
    50                  55                  60

Ser Asp Pro Cys Ala Ala Leu Ser Val Val Phe Asp Lys Gly Val
65                  70                  75                  80

Leu Glu Gln Ile Cys Glu Gly Lys Gly Tyr Ile Asp Met Ser Thr Val
                85                  90                  95

Asp Ala Glu Thr Ser Leu Lys Ile Asn Glu Ala Ile Thr Gly Lys Gly
            100                 105                 110

Gly Arg Phe Val Glu Gly Pro Val Ser Gly Ser Lys Lys Pro Ala Glu
        115                 120                 125

Asp Gly Gln Leu Ile Ile Leu Ala Ala Gly Asp Lys Ala Leu Phe Glu
    130                 135                 140

Glu Ser Ile Pro Ala Phe Asp Val Leu Gly Lys Arg Ser Phe Tyr Leu
145                 150                 155                 160

Gly Gln Val Gly Asn Gly Ala Lys Met Lys Leu Ile Val Asn Met Ile
                165                 170                 175

Met Gly Ser Met Met Asn Ala Phe Ser Glu Gly Leu Val Leu Ala Asp
            180                 185                 190

Lys Ser Gly Leu Ser Ser Asp Thr Leu Leu Asp Ile Leu Asp Leu Gly
        195                 200                 205

Ala Met Thr Asn Pro Met Phe Lys Gly Lys Gly Pro Ser Met Thr Lys
    210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val Ile Glu Ala Val Lys Phe Ser Arg
        275                 280                 285

Glu
```

<210> SEQ ID NO 5
<211> LENGTH: 1680
<212> TYPE: DNA
<213> ORGANISM: Pseudomonas putida

<400> SEQUENCE: 5

```
atgagtaaca agaacaacga tgagctgcag tggcaatcct ggttcagcaa ggcgcccacc      60
accgaggcga acccgatggc caccatgttg caggatatcg gcgttgcgct caaaccggaa     120
gcgatggagc agctgaaaaa cgattatctc cgtgacttca ccgcgttgtg caggattttt     180
ttggctggca aggcgccagc cgtcagcgac cgccgcttca gctcggcagc ctggcagggc     240
```

```
aatccgatgt cggccttcaa tgccgcatct tacctgctca acgccaaatt cctcagtgcc    300
atggtggagg cggtggacac cgcaccccag caaaagcaga aaatacgctt tgccgtgcag    360
caggtgattg atgccatgtc gcccgcgaac ttcctcgcca ccaacccgga agcgcagcaa    420
aaactgattg aaaccaaggg cgagagcctg acgcgtggcc tggtcaatat gctgggcgat    480
atcaacaagg ccatatctc gctgtcggac gaatcggcct ttgaagtggg ccgcaacctg    540
gccattaccc cgggcaccgt gatttacgaa aatccgctgt tccagctgat ccagtacacg    600
ccgaccacgc cgacggtcag ccagcgcccg ctgttgatgg tgccgccgtg catcaacaag    660
ttctacatcc tcgacctgca accggaaaat tcgctggtgc gctacgcggt ggagcagggc    720
aacaccgtgt tcctgatctc gtggagcaat ccggacaagt cgctggccgg caccacctgg    780
gacgactacg tggagcaggg cgtgatcgaa gcgatccgca tcgtccagga cgtcagcggc    840
caggacaagc tgaacatgtt cggcttctgc gtgggcggca ccatcgttgc caccgcactg    900
gcggtactgg cggcgcgtgg ccagcacccg gcggccagcc tgaccctgct gaccaccttc    960
ctcgacttca gcgacaccgg cgtgctcgac gtcttcgtcg atgaaaccca ggtcgcgctg   1020
cgtgaacagc aattgcgcga tggcggcctg atgccgggcc gtgacctggc ctcgaccttc   1080
tcgagcctgc gtccgaacga cctggtatgg aactatgtgc agtcgaacta cctcaaaggc   1140
aatgagccgg cggcgtttga cctgctgttc tggaattcgg acagcaccaa tttgccgggc   1200
ccgatgttct gctggtacct gcgcaacacc tacctggaaa acagcctgaa agtgccgggc   1260
aagctgacgg tggccggcga aaagatcgac ctcggcctga tcgacgcccc ggccttcatc   1320
tacggttcgc gcgaagacca catcgtgccg tggatgtcgg cgtacggttc gctcgacatc   1380
ctcaaccagg gcaagccggg cgccaaccgc ttcgtgctgg gcgcgtccgg ccatatcgcc   1440
ggcgtgatca actcggtggc caagaacaag cgcagctact ggatcaacga cggtggcgcc   1500
gccgatgccc aggcctggtt cgatggcgcg caggaagtgc cgggcagctg gtggccgcaa   1560
tgggccgggt cctgacccca gcatggcggc aagaaggtca agcccaaggc caagcccggc   1620
aacgcccgct acaccgcgat cgaggcggcg cccggccgtt acgtcaaagc caagggctga   1680
```

<210> SEQ ID NO 6
<211> LENGTH: 559
<212> TYPE: PRT
<213> ORGANISM: Pseudomonas putiza

<400> SEQUENCE: 6

```
Met Ser Asn Lys Asn Asn Asp Glu Leu Gln Trp Gln Ser Trp Phe Ser
1               5                   10                  15

Lys Ala Pro Thr Thr Glu Ala Asn Pro Met Ala Thr Met Leu Gln Asp
                20                  25                  30

Ile Gly Val Ala Leu Lys Pro Glu Ala Met Glu Gln Leu Lys Asn Asp
            35                  40                  45

Tyr Leu Arg Asp Phe Thr Ala Leu Trp Gln Asp Phe Leu Ala Gly Lys
        50                  55                  60

Ala Pro Ala Val Ser Asp Arg Arg Phe Ser Ser Ala Ala Trp Gln Gly
65                  70                  75                  80

Asn Pro Met Ser Ala Phe Asn Ala Ala Ser Tyr Leu Leu Asn Ala Lys
                85                  90                  95

Phe Leu Ser Ala Met Val Glu Ala Val Asp Thr Ala Pro Gln Gln Lys
            100                 105                 110

Gln Lys Ile Arg Phe Ala Val Gln Gln Val Ile Asp Ala Met Ser Pro
        115                 120                 125
```

```
Ala Asn Phe Leu Ala Thr Asn Pro Glu Ala Gln Gln Lys Leu Ile Glu
130                 135                 140

Thr Lys Gly Glu Ser Leu Thr Arg Gly Leu Val Asn Met Leu Gly Asp
145                 150                 155                 160

Ile Asn Lys Gly His Ile Ser Leu Ser Asp Glu Ser Ala Phe Glu Val
                165                 170                 175

Gly Arg Asn Leu Ala Ile Thr Pro Gly Thr Val Ile Tyr Glu Asn Pro
                180                 185                 190

Leu Phe Gln Leu Ile Gln Tyr Thr Pro Thr Thr Pro Thr Val Ser Gln
            195                 200                 205

Arg Pro Leu Leu Met Val Pro Pro Cys Ile Asn Lys Phe Tyr Ile Leu
        210                 215                 220

Asp Leu Gln Pro Glu Asn Ser Leu Val Arg Tyr Ala Val Gln Gly
225                 230                 235                 240

Asn Thr Val Phe Leu Ile Ser Trp Ser Asn Pro Asp Lys Ser Leu Ala
                245                 250                 255

Gly Thr Thr Trp Asp Asp Tyr Val Glu Gln Gly Val Ile Glu Ala Ile
                260                 265                 270

Arg Ile Val Gln Asp Val Ser Gly Gln Asp Lys Leu Asn Met Phe Gly
            275                 280                 285

Phe Cys Val Gly Gly Thr Ile Val Ala Thr Ala Leu Ala Val Leu Ala
        290                 295                 300

Ala Arg Gly Gln His Pro Ala Ala Ser Leu Thr Leu Leu Thr Thr Phe
305                 310                 315                 320

Leu Asp Phe Ser Asp Thr Gly Val Leu Asp Val Phe Val Asp Glu Thr
                325                 330                 335

Gln Val Ala Leu Arg Glu Gln Gln Leu Arg Asp Gly Gly Leu Met Pro
                340                 345                 350

Gly Arg Asp Leu Ala Ser Thr Phe Ser Ser Leu Arg Pro Asn Asp Leu
            355                 360                 365

Val Trp Asn Tyr Val Gln Ser Asn Tyr Leu Lys Gly Asn Glu Pro Ala
        370                 375                 380

Ala Phe Asp Leu Leu Phe Trp Asn Ser Asp Ser Thr Asn Leu Pro Gly
385                 390                 395                 400

Pro Met Phe Cys Trp Tyr Leu Arg Asn Thr Tyr Leu Glu Asn Ser Leu
                405                 410                 415

Lys Val Pro Gly Lys Leu Thr Val Ala Gly Glu Lys Ile Asp Leu Gly
                420                 425                 430

Leu Ile Asp Ala Pro Ala Phe Ile Tyr Gly Ser Arg Glu Asp His Ile
            435                 440                 445

Val Pro Trp Met Ser Ala Tyr Gly Ser Leu Asp Ile Leu Asn Gln Gly
        450                 455                 460

Lys Pro Gly Ala Asn Arg Phe Val Leu Gly Ala Ser His Ile Ala
465                 470                 475                 480

Gly Val Ile Asn Ser Val Ala Lys Asn Lys Arg Ser Tyr Trp Ile Asn
                485                 490                 495

Asp Gly Gly Ala Ala Asp Ala Gln Ala Trp Phe Asp Gly Ala Gln Glu
            500                 505                 510

Val Pro Gly Ser Trp Trp Pro Gln Trp Ala Gly Phe Leu Thr Gln His
        515                 520                 525
```

```
Gly Gly Lys Lys Val Lys Pro Lys Ala Lys Pro Gly Asn Ala Arg Tyr
    530             535             540

Thr Ala Ile Glu Ala Ala Pro Gly Arg Tyr Val Lys Ala Lys Gly
545             550             555
```

LOW-TEMPERATURE PROCESSABLE ALIPHATIC POLYESTER

FIELD OF THE INVENTION

The present invention relates to a low-temperature processible aliphatic polyester in which physical properties such as elasticity and transparency are adjusted.

BACKGROUND OF THE INVENTION

Currently, the use of biodegradable polymers is more demanding than ever before in the world. For this reason, the problem of the plastic waste disposal has emerged as a national issue and the seriousness of the problem is frequently reported through the media, which requires a fundamental solution to such seriousness more than ever. Further, legislation is under way to enforce government-led regulatory policies or restrictions on the use of synthetic plastics (The EU has already partially been implementing some items such as biodegradable bags). Above all, what is emerging as a serious problem is that the environmental pollution caused by microplastics is adversely affecting the marine ecosystem, which has been continuously pointed out as an issue since the last five years.

The material which has currently been developed to solve these problems is aliphatic polyester of polyhydroxyalkanoate, in particular, a random binary system copolymer having two monomers of 3-hydroxybutryates (3HB) and 4-hydroxybutyrates (4-HB) as basic repeated structures. These polymers have the characteristics that the mechanical and thermal properties thereof change greatly depending on change in the molecular weight and a rate of the 4-hydroxybutryates. Above all, the polyhydroxyalkanoate has the same mechanical and thermal properties as synthetic polymers, and has the advantage that can be biodegraded so that it will be fully available as an alternative to solve the conventional problems. Therefore, a research is actively underway to develop biopolymers that are compostable at home, compostable in seawater and 100% biodegradable by utilizing the characteristics of the polymers.

SUMMARY OF THE INVENTION

The present invention relates to a low-temperature processible aliphatic polyester and provides a polymer material comprising a polyhydroxyalkanoate copolymer having an adjusted content of 4-hydroxybutyrates (4HB).

By utilizing the polymer material according to the present invention, the polymer material can serve as a binder as a short-term biological support, and can be applied as a hot melt material and a non-woven cloth material to impart tacky function to a material that is very sensitive to heat. In addition, the polymer material can be easily applied to various fields.

The graph shows an elastic zone around 10% of the strain, a decrease in the stress over a yield point followed by a necking phenomenon (the phenomenon of a polymer expanding locally under a tensile stress), and then shows a constant tensile strength. As the chain orientation approaches its extreme point, the graph shows a curve in which the tensile strength increases beyond the yield tension strength, and then breaks.

Figure 2:
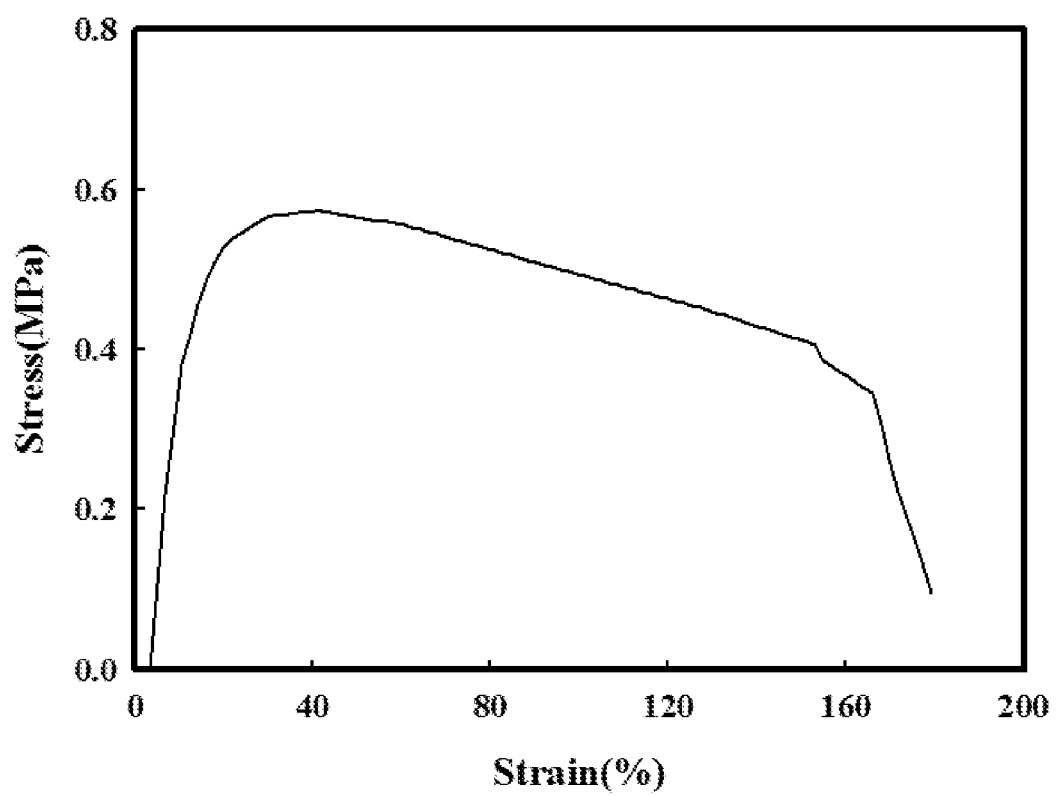

FIG. 2 is a graph showing a stress of a sample against a strain of PHA having a 4HB content of 50% according to the present invention. The curve of the graph initially shows a maximum tensile strength without any remarkable yield point followed by a necking phenomenon, and shows the tendency to break with decrease in the tensile strength.

Figure 3:
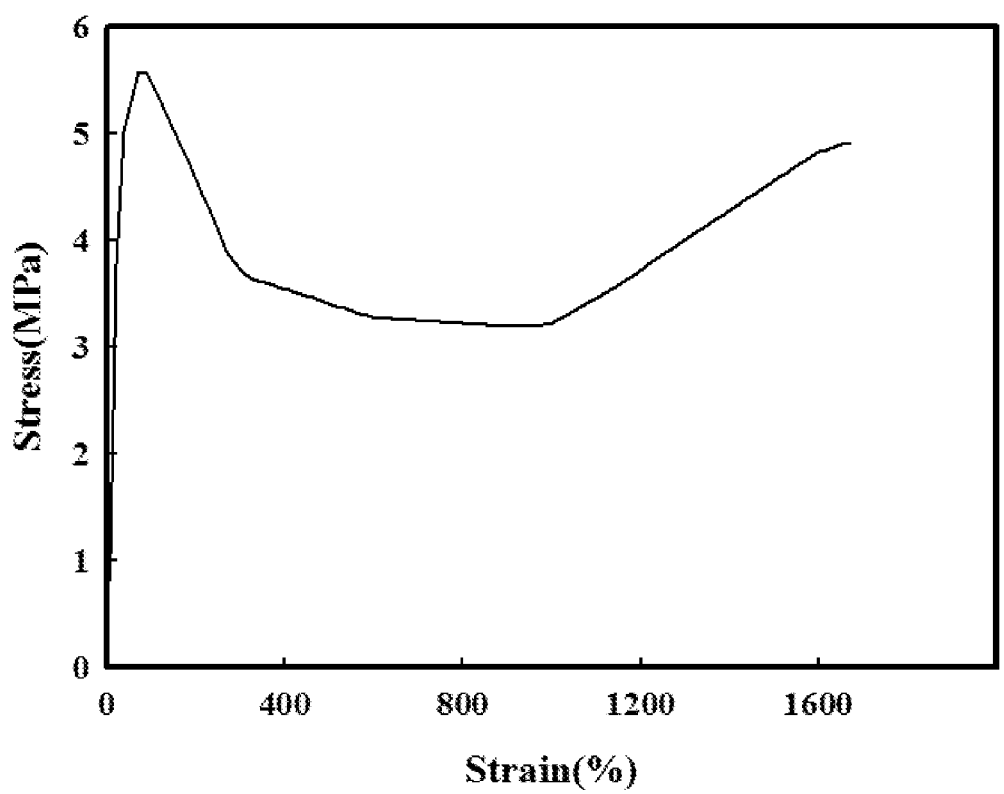

FIG. 3 is a graph showing a stress of a sample against a strain of PHA having a 4HB content of 90% according to the present invention. The graph shows the tendency of indicating a yield point at 80% of the strain followed by a necking phenomenon and decrease in a tensile strength. As the chain orientation approaches its extreme point, the tensile strength increases, and a break occurs before the yield tensile strength.

DETAILED DESCRIPTION OF THE INVENTION

The present invention will be described in detail as follows.

Meanwhile, each of the descriptions and embodiments disclosed in the present invention may be applied to each of other descriptions and embodiments. That is, all combinations of the various constitutive elements disclosed in the present invention fall within the scope of the present invention. Further, it is not intended that the scope of the present invention be limited by the detailed descriptions disclosed below. Furthermore, if it is determined that the detailed description of the related known technology in the present invention may obscure the gist of the present invention, the detailed description thereof will be omitted.

In the present specification, the singular expressions "a", "an" and "the" may imply plural expressions unless otherwise specified.

Unless stated otherwise in the present specification, the expression "to" is used as an expression including a corresponding numerical value. Specifically, for example, the expression "1 to 2" may mean not only including 1 and 2, but also including all numerical values between 1 and 2.

The term "PHA copolymer" herein means a polymer consisting of at least two different hydroxyalkanoic acid monomers.

A polyhydroxyalkanoate copolymer composition is provided. The composition comprises a plurality of polyhydroxyalkanoate copolymer molecules. The composition can be, for example, a biomass composition, e.g. an organism that has produced, and comprises therein, the plurality of polyhydroxyalkanoate copolymer molecules, a composition free of non-polyhydroxyalkanoate biomass, e.g. a composition comprising polyhydroxyalkanoate copolymer molecules that have been isolated and/or purified from an organism that has produced the polyhydroxyalkanoate copolymer molecules, or a bioplastic composition, e.g. a homogeneous or blended composition comprising the polyhydroxyalkanoate copolymer molecules and suitable for use as a bioplastic.

The polyhydroxyalkanoate copolymer molecules comprise 3-hydroxybutyrate monomers and 4-hydroxybutyrate monomers. Accordingly, each polyhydroxyalkanoate copolymer molecule comprises both 3-hydroxybutyrate monomers and 4-hydroxybutyrate monomers. Such molecules can be synthesized, for example, by PHA-synthase mediated copolymerization of 3-hydroxybutyryl-CoA and 4-hydroxybutyryl-CoA to yield molecules of the copolymer, e.g. poly(3-hydroxybutyrate-co-4-hydroxybutyrate) copolymer.

The polymer materials according to the present invention are capable of both of 100% biodegradation and composting by adjusting a ratio of 4-hydroxybutryates (4HB) in a total polymer repeated structure to a high content, and in particular, can be processed at a low temperature of 100° C. or less. In particular, they can have a melting property at a body temperature and can be biodegraded.

The polyhydroxyalkanoate copolymer molecules have a monomeric molar percentage of 4-hydroxybutyrate monomers of 76 to 98%. Therefore, a content of the remaining monomers containing 3-hydroxybutyrate monomers is 2 to 24%. Further, for example, the content of 4-hydroxybutyrate monomers may be 80 to 95 mol %, for example, 82 mol % or more, 85 mol % or more, or 90 mol % or more, or, for example, 95 mol % or less, or 93 mol % or less.

According to an embodiment, ≥95% or ≥99%, of the remaining 2 to 24% of the monomeric units correspond to 3-hydroxybutyrate monomers, with the rest corresponding to further additional monomers.

In some embodiments, all of the remaining 2 to 24% of the monomeric units correspond to 3-hydroxybutyrate monomers, such that the polyhydroxyalkanoate copolymer molecules include no further additional monomers. Thus, for example with regard to poly(3-hydroxybutyrate-co-4-hydroxybutyrate) copolymer, in particular, for polyhydroxyalkanoate copolymer molecules having a monomeric molar percentage of 4-hydroxybutyrate monomers of 76 to 98%, the remaining 2 to 24% of the monomeric units of the polyhydroxyalkanoate copolymer molecules correspond to 3-hydroxybutyrate monomers.

According to an embodiment, the polymer materials according to the present invention may have a ratio of 4-hydroxybutryates (4-HB) in the total polymer repeated structure in the range of, for example, 76% or more, 80% or more, or 90% or more, for example, 98% or less, 95% or less, or 93% or less, so as to enhance physical properties such as color difference, elasticity, low-temperature processing, and biodegradation.

The monomeric molar percentages of 4-hydroxybutyrate monomers of polyhydroxyalkanoate copolymer molecules affect properties of compositions thereof, for example with respect to melting temperatures, elongation to break, glass transition temperatures, and the like. Thus, polyhydroxyalkanoate copolymer molecules having monomeric molar percentages of 4-hydroxybutyrate monomers in each of the various ranges disclosed above can be used to engineer compositions to have particular desired properties.

The polyhydroxyalkanoate copolymer molecules have a biobased content of ≥50%, for example, ≥80%. Biobased content, as the term is used herein, means the amount of biobased carbon in a material or product as a percent of the weight (mass) of the total organic carbon of the material or product, as defined in ASTM D6866-12, Standard Test Methods for Determining the Biobased Content of Solid, Liquid, and Gaseous Samples Using Radio carbon Analysis (ASTM International, U.S., 2012), which is incorporated by reference herein. As discussed in ASTM D6866-12, total organic carbon can include both biobased carbon and fossil carbon. Biobased carbon corresponds to organic carbon that includes radiocarbon, i.e. $^{14}C$, in an amount indicative of recent cycling through the living biosphere, e.g. recent incorporation of atmospheric $CO_2$, including a known percentage of $^{14}C$, into organic carbon. Fossil carbon corresponds to organic carbon that includes little or no radiocarbon because the age of the fossil carbon, as measured from the date of incorporation of atmospheric $CO_2$, is much greater than the half-life of $^{14}C$, i.e. all or essentially all of the $^{14}C$ that had been incorporated has decayed. Accordingly, as applied to polyhydroxyalkanoate copolymer molecules, biobased content means the amount of biobased carbon in the polyhydroxyalkanoate copolymer molecules as a percent of the weight (mass) of the total organic carbon of the polyhydroxyalkanoate copolymer molecules. The biobased content of the polyhydroxyalkanoate copolymer molecules can be measured, for example, in accordance with ASTM D6866-12, based on determining the contents of $^{14}C$ and $^{12}C$ in $CO_2$ derived by combustion of the polyhydroxyalkanoate, and correcting for post 1950 bomb $^{14}C$ injection into the atmosphere, among other methods. Thus, for example, the polyhydroxyalkanoate copolymer molecules can have a biobased content of ≥50%, for example ≥80% as measured in accordance with ASTM D6866-12. Other suitable approaches for measuring biobased content, as are known in the art, also can be used. Differences in biobased contents between different polyhydroxyalkanoate copolymer molecules are indicative of structural differences, i.e. differences in the ratios of $^{14}C$ to $^{12}C$ thereof, between the different polyhydroxyalkanoate copolymer molecules.

According to an embodiment, the biobased content of the polyhydroxyalkanoate copolymer molecules according to the present invention is, for example, 50% or more, 80% or more, 90% or more, 95% or more, or 100%, according to ASTM D6866-12.

The polyhydroxyalkanoate copolymer molecules having the above-noted biobased content can be used for the manufacture of biobased plastics in which most or all fossil carbon has been replaced by renewable biobased carbon, with accompanying environmental benefits. Moreover, the polyhydroxyalkanoate copolymer molecules having the above-noted biobased contents can be distinguished readily from polyhydroxyalkanoate copolymer molecules and other polymers and compounds not having the above-noted biobased contents, based on the above-noted structural differences associated with differences in biobased contents, with accompanying regulatory benefits.

A weight average molecular weight of the polyhydroxyalkanoate copolymer molecules of the present invention may be, for example, 200 kDa or more, 250 kDa or more, 300 kDa or more, 400 kDa or more, or 440 kDa or more, for example, 2 MDa or less, 1 MDa or less, 800 kDa or less, 700 kDa or less, 600 kDa or less, or 570 kDa or less. Moreover, the weight average molecular weight can, for example, be determined by use of a gel permeation chromatography with polystyrene standards.

The polyhydroxyalkanoate copolymer molecules can occur in a distribution with respect to their molecular weights, and the physical properties and rheological properties of compositions of the polyhydroxyalkanoate copolymer molecules can depend on the distribution. Molecular weights of polymers can be calculated various ways. A weight average molecular weight, also termed $M_w$, is the sum of the weights of the various chain lengths, times the molecular weight of the chain, divided by the total weight of all of the chains ($\Sigma N_i M_i^2 / \Sigma N_i M_i$). A number average molecular weight, also termed $M_n$, is the sum of the number of chains of a given length, times the molecular weight of the chain, divided by the total number of chains ($\Sigma N_i M_i / \Sigma N_i$). A polydispersity index provides a measure of the broadness of a molecular weight distribution of a polymer and is calculated as the weight average molecular weight divided by the number average molecular weight. As used herein, the term molecular weight refers to weight average molecular weight unless context indicates otherwise.

The weight average molecular weight of polyhydroxyalkanoate copolymer molecules can be determined, for example, by use of gel permeation chromatography with polystyrene standards. Chloroform can be used as both the eluent for the gel permeation chromatography and as the eluent for the polyhydroxyalkanoates. Calibration curves for determining the molecular weights can be generated by using linear polystyrenes as molecular weight standards and a calibration method based on log molecular weight as a function of elution volume.

According to an embodiment, a melting point (Tm) of the polyhydroxyalkanoate copolymer molecules of the present invention may be 30 to 100° C., for example 35° C. or more, or, for example, 80° C. or less, 70° C. or less, 60° C. or less, or 55 or less. The melting point may be measured by Differential Scanning Calorimetry (DSC).

According to an embodiment, a decomposition temperature (Td) of the polyhydroxyalkanoate copolymer molecules of the present invention may be 200 to 400° C., for example, 230° C. or more, or 280° C. or more, or, for example 350° C. or less, or 330° C. or less. The decomposition temperature can be measured by Thermal Gravimetric Analysis (TGA).

According to an embodiment, an acid value of the polyhydroxyalkanoate copolymer molecules of the present invention may be 0.5 to 4.5, for example, 0.8 or more, or 1 or more, or, for example, 4 or less, 3 or less, or 2 or less, for example, 0.5 to 2. The acid value may be expressed in mg number of a potassium hydroxide required to neutralize a free fatty acid contained in 1 g of a sample.

According to an embodiment, the color difference of the polyhydroxyalkanoate copolymer molecules of the present invention may be 1 to 15, for example, 3 or more, or 5 or more, or, for example, 13 or less, or 12 or less, for example, 1 to 12.

According to an embodiment, a melt flow index (MFI) of the polyhydroxyalkanoate copolymer molecules of the present invention may be 3 to 10, for example, 4.5 or more, or 5 or more, or, for example, 8 or less, or 6 or less.

According to an embodiment, an elongation of the polyhydroxyalkanoate copolymer molecules of the present invention may range from 1000 to 2500%, for example, 1000% or more, 1300% or more, 1500% or more, or 1700% or more, or, for example, 2500% or less, 2000% or less, or 1900% or less, for example, from 1000 to 2000% or from 1700 to 1900%.

According to an embodiment, the tensile strength of the polyhydroxyalkanoate copolymer molecule of the present invention may be 1 to 20 MPa, for example, 3 MPa or more, or 5 MPa or more, or, for example 15 MPa or less, or 10 MPa or less, for example, 5 to 20 MPa or 5 to 8 MPa.

The elongation and the tensile strength can be measured on a 300-micron thickness sheet, for example, in accordance with ASTM-D882.

According to an embodiment, a refractive index ($nD^{25}$) of the polyhydroxyalkanoate copolymer molecules of the present invention may be 1.3 to 1.7, for example, 1.4 or more, 1.45 or more, or 1.48 or more, or, for example, 1.6 or less, 1.5 or less, or 1.49 or less, for example, 1.3 to 1.5. The refractive index ($nD^{25}$) can be measured based on 25 micron film.

The composition can be one wherein the monomeric molar percentage of 4-hydroxybutyrate monomers of the polyhydroxyalkanoate copolymer molecules does not decrease with increasing molecular weight of the polyhydroxyalkanoate copolymer molecules. As noted above, the polyhydroxyalkanoate copolymer molecules can occur in a distribution with respect to their molecular weights. The monomeric molar percentages of 4-hydroxybutyrate monomers may vary between individual polyhydroxyalkanoate copolymer molecules. A composition wherein the monomeric molar percentage of 4-hydroxybutyrate monomers of the polyhydroxyalkanoate copolymer molecules does not decrease with increasing molecular weight of the polyhydroxyalkanoate copolymer molecules can be, for example, a composition wherein the monomeric molar percentage of 4-hydroxybutyrate monomers of polyhydroxyalkanoate copolymer molecules at the high end of the molecular weight distribution is not lower than the monomeric molar percentage of 4-hydroxybutyrate monomers of polyhydroxyalkanoate copolymer molecules at the low end of the molecular weight distribution. Thus, for example, the composition can be one wherein the monomeric molar percentage of 4-hydroxybutyrate monomers of the polyhydroxyalkanoate copolymer molecules does not vary substantially, e.g. at all, with increasing molecular weight of the polyhydroxyalkanoate copolymer molecules, e.g. the monomeric molar percentage of 4-hydroxybutyrate monomers of polyhydroxyalkanoate copolymer molecules at the high end of the molecular weight distribution is essentially the same, e.g. identical, to th at of polyhydroxyalkanoate copolymer molecules at the low end of the molecular weight distribution. Also for example, the composition can be one wherein the monomeric molar percentage of 4-hydroxybutyrate monomers of the polyhydroxyalkanoate copolymer molecules increases with increasing molecular weight of the polyhydroxyalkanoate copolymer molecules, e.g. the monomeric molar percentage of 4-hydroxybutyrate monomers of polyhydroxyalkanoate copolymer molecules at the high end of the molecular weight distribution is higher than that of polyhydroxyalkanoate copolymer molecules at the low end of the molecular weight distribution.

The composition can be one wherein the polyhydroxyalkanoate copolymer molecules are produced in a fermentation process using one or more carbon raw materials that, taken together, have a biobased content of ≥50%, for example, ≥80%; the one or more carbon raw materials comprise a carbon source selected from the group consisting of molasses, starch, a fatty acid, a vegetable oil, a lignocellulosic material, ethanol, acetic acid, glycerol, a biomass-derived synthesis gas, and methane originating from a landfill gas, glucose, levoglucosan, sucrose, lactose, fructose, xylose, maltose, arabinose, and mixtures thereof; and the yield is greater than 0.25 g of the polyhydroxyalkanoate copolymer molecules per gram of the carbon source. For example, in some embodiments the yield is greater than 0.30 g, or greater than 0.35 g, or greater than 0.40 g, of the polyhydroxyalkanoate copolymer molecules per gram of the carbon source.

As noted, the polyhydroxyalkanoate copolymer molecules are present at ≥50 weight percent of the biomass composition. As used herein, weight percent of the biomass composition refers to dry weight of the biomass composition, e.g. cell dry weight. The polyhydroxyalkanoate copolymer molecules can be present, for example, at ≥60, ≥70, ≥80, ≥85, or ≥90 weight percent of the biomass composition.

The method can comprise culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the composition.

The culturing can comprise, for example, cultivating the organism by fermentation, shake-flask cultivation, and the like. Fermentation can be carried out, for example, at scales ranging from laboratory scale, e.g. 1 L, to industrial manufacturing scale, e.g. 20,000 to 100,000 L.

The organism can be, for example, a microbial strain or an algal strain. Suitable microbial strains include, for example, an *Escherichia coli* strain or a *Ralstonia eutropha* strain. Suitable algal strains include, for example, a *Chlorella* strain. Additional suitable organisms are described in the Examples below.

The one or more carbon raw materials can comprise a carbon raw material that can be used in an industrial process, e.g. to supply a carbon or other energy source for cells of a fermentation process, and/or that is renewable, e.g. material derived from living organisms or their metabolic byproducts including material derived from biomass, often consisting of underutilized components like chaff or stover. For example, the one or more carbon raw materials can comprise a carbon source selected from the group consisting of glucose, levoglucosan, sucrose, lactose, fructose, xylose, maltose, arabinose, and mixtures thereof. Also, for example, the one or more carbon raw materials can comprise one or more of molasses, starch, a fatty acid, a vegetable oil, a lignocellulosic material, ethanol, acetic acid, glycerol, a biomass-derived synthesis gas, and methane originating from a landfill gas.

Considering the one or more carbon raw materials further, in some embodiments, the one or more carbon raw materials can consist essentially of a carbon source selected from the group consisting of glucose, levoglucosan, sucrose, lactose, fructose, xylose, maltose, arabinose, and mixtures thereof. In some embodiments, the one or more carbon raw materials can consist of a carbon source selected from the group consisting of glucose, levoglucosan, sucrose, lactose, fructose, xylose, maltose, arabinose, and mixtures thereof. Thus, in some embodiments the one or more carbon raw materials can consist essentially of a single carbon source, e.g. glucose. Also, in some embodiments the one or more carbon raw materials can consist of a single carbon source, again e.g. glucose.

The one or more carbon raw materials can also exclude particular compounds, such as compounds that are immediate precursors of 4-hydroxybutyryl-CoA and/or compounds that are typically manufactured from nonrenewable resources, e.g. from petroleum, based on substantially lower cost in comparison to manufacture thereof from renewable resources, e.g. crops. Incorporation of such compounds for production of polyhydroxyalkanoate copolymer molecules can be costly, particularly with respect to industrial manufacturing scale, e.g. by fermentation using 20,000 to 100,000 L vessels, based on requiring additional feeds and thus infrastructure and quality control, and can result in a need for tighter control in order to achieve polyhydroxyalkanoate copolymer compositions with structural consistency. The one or more carbon raw materials can be, for example, ones that do not comprise γ-butyrolactone, 1,4-butanediol, 4-hydroxybutyrate, 3-hydroxybutyrate, α-ketoglutarate, oxaloacetate, malate, fumarate, citrate, succinate, or 3-hydroxybutyrate, and thus that exclude each of these compounds. Thus, for example, the culturing of the organism can be carried out in the absence of γ-butyrolactone, 1,4-butanediol, 4-hydroxybutyrate, 3-hydroxybutyrate, α-ketoglutarate, oxaloacetate, malate, fumarate, citrate, succinate, and 3-hydroxybutyrate, i.e. without adding any of these compounds exogenously before, during, or after the culturing.

The conditions can be conditions that are suitable, e.g. typical and/or optimal, for cultivation of the organism, e.g. with respect to temperature, oxygenation, initial titer of the organism, time of cultivation, etc. Exemplary suitable conditions are provided in the Examples below.

The one or more carbon raw materials can be converted to 3-hydroxybutyryl-CoA and 4-hydroxybutyryl-CoA by enzymes expressed by the organism. The 3-hydroxybutyryl-CoA and the 4-hydroxybutyryl-CoA also can be polymerized to form the polyhydroxyalkanoate copolymer molecules, thereby forming the composition, by enzymes expressed by the organism.

In accordance with the method, the organism has been genetically engineered to comprise enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase, and to not comprise enzymatic activities of either an NAD+-dependent succinate-semialdehyde dehydrogenase or an NADP+-dependent succinate-semialdehyde dehydrogenase or both.

The organism can be genetically engineered to comprise the enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase, for example, by transforming the organism with one or more genes encoding each of the enzymatic activities. For example, the genes can be stably incorporated into the organism, e.g. by introduction on one or more stable plasmids and/or by integration into the genome of the organism. The organism can also be genetically engineered to comprise the enzymatic activities, for example, by altering the promoter regions of one or more genes encoding each of the enzymatic activities, for example by replacing naturally occurring promoters with stronger promoters and/or by eliminating repressor sequences. In addition, combinations of these approaches and the like can be used. Using approaches such as these can result in integration of the genes in the organism with high stability, e.g. greater than 50 generations of the organism, and high expression, sufficient for industrial production, for example, by fermentation using 20,000 to 100,000 L vessels. Suitable exemplary approaches are discussed in more detail below.

The organism also can be genetically engineered to not comprise enzymatic activities of either an NAD+-dependent succinate-semialdehyde dehydrogenase or an NADP+-dependent succinate-semialdehyde dehydrogenase or both, for example, by introducing one or more inhibitory mutations or sequences in the organism to inhibit expression of either or both activities, by deleting from the genome of the organism the corresponding genes that encode either or both activities, by disrupting either or both of the corresponding genes partially or completely by homologous recombination, and/or by interfering with expression of either or both of the corresponding genes such as by expressing siRNAs that interfere with expression of the corresponding genes. Suitable exemplary approaches are discussed in more detail below.

In accordance with the method, the organism can further be genetically engineered to comprise enzymatic activities of an alpha-ketoglutarate decarboxylase or 2-oxoglutarate decarboxylase, and an L-1,2-propanediol oxidoreductase. The organism also can be genetically engineered to not comprise enzymatic activities of one or more of a thioesterase II, a multifunctional acyl-CoA thioesterase I and protease I and lysophospholipase L, an acyl-CoA thioesterase, and an aldehyde dehydrogenase.

The method can also comprise isolating the polyhydroxyalkanoate copolymer molecules from the organism, such that the polyhydroxyalkanoate copolymer composition is substantially free of the organism. Suitable exemplary approaches for such isolation are known in the art.

According to an embodiment, the present invention provides a low-temperature processable aliphatic polyester prepared in accordance with the method as described above. The low-temperature processable aliphatic polyester of the present invention may contain a content of 4-hydroxybutyrate monomers of 76 to 98 mol % with the fermentation of a strain.

Since the polymer materials according to the present invention can effectively lower a temperature of the melting point (Tm) compared to the conventional materials, they can serve as a binder as a short-term biological support, and can be applied as a hot melt material and a non-woven cloth material for imparting tacky function to a material that is very sensitive to heat. In addition, they can be easily applied to a field that is sensitive to heat and a field requiring the low-temperature processibility.

Specifically, the present invention can be used for a hot melt adhesive, a reactive hot melt adhesive, a biodegradable wax, a medical device, a low-temperature hot melt, a non-woven cloth, a bioplastic, a drug carrier, a medical wrap, a medical fiber, a medical filament, a medical stent, or an orthopedic prosthesis.

According to an embodiment, the hot melt adhesive or the reactive hot melt adhesive of the present invention may contain the polyhydroxyalkanoate according to the present invention in an amount of 0.1 to 90% by weight, for example, 1% by weight or more, 5% by weight or more, 10% by weight or more, 20% by weight or more, 30% by weight or more, or 40% by weight or more, or, for example, 80% by weight or less, 70% by weight or less, or 50% by weight or less, based on the total weight of the hot melt adhesive composition.

According to an embodiment, the biodegradable wax composition of the present invention may contain other components such as at least one wax component together with the polyhydroxyalkanoate oligomer.

According to an embodiment, the hot melt adhesive composition of the present invention may optionally contain at least one or more of a reactive monomer or oligomer component, a wax component, a tackifying resin and other additives. According to an embodiment, the reactive monomer or oligomer may be contained in an amount of about 5 to about 95% by weight, for example, about 35 to about 55% by weight, based on the total weight of the hot melt adhesive composition of the present invention.

Further, for example, the tackifying resin may be contained in 60% by weight or less of the hot melt adhesive composition, and the wax component may be contained in 40% by weight or less. Specifically, the wax component may, for example, include a functionalized wax such as a paraffin wax, a microcrystalline wax, a high density low molecular weight polyethylene wax, a by-product polyethylene wax, a Fischer-Tropsch wax, an oxidized Fischer-Tropsch wax, a hydrokinesis stearamide wax, a fatty acid amide wax, and a synthetic high melting point wax. Examples of the high density low molecular weight polyethylene wax may include, Polywax™500, Polywax™1500 and Polywax™2000, which are ethylene homopolymers available from Petrolite, Inc. (Tulsa, Okla.). The Polywax™2000 has a molecular weight of about 2000, Mw/Mn of about 1.0, a density of about 0.97 g/cm$^3$ at 16° C., and a melting point of about 126° C. The paraffin wax has a softening point of about 55° C. to about 85° C. by a circulating method, and may include, for example, Okerin R236TP available from Astor Wax Corporation located at Doraville, Ga.; Penreco R4913 available from Pennzoil Products Co. in Houston, Tex.; R-7152 Paraffin Wax available from Moore & Munger in Shelton, Conn.; and Paraffin Wax1297 available from International Waxes, Ltd. in Ontario, Canada. Examples of still other paraffin wax may include, for example, waxes available from CP Hall under product numbers 1230, 1236, 1240, 1245, 1246, 1255, 1260 and 1262. In addition, the microcrystalline wax may include those having 50% by weight or more of cyclic or branched alkane with a carbon length of 30 to 100.

They are generally less crystalline than the paraffin and polyethylene waxes and have a melting point greater than about 70° C. Examples of them may include VictoryR, Amber Wax, a wax of melting point 70° C. available from Petrolite Corp. in Tulsa, Okla.; BarecoRBS-796 Amber Wax, a wax of melting point 70° C. available from Bareco, Chicago, Ill.; Okerin R177, a wax of melting point 80° C. available from Astor Wax Corp.; BesquareR175 and 195 Amber Wax, microcrystalline waxes of melting points 80° C. and 90° C. available from Petrolite Corp. in Tulsa, Okla.; Indramic R91, a wax of melting point 90° C. available from Industrial Raw Materials in Smethport, Pa.; and Petrowax R9508Light, a wax of melting point 90° C. available from Petrowax PA. Inc. in New York, N.Y. Further, the synthetic high melting point (HMP) waxes may include the high density low molecular weight polyethylene wax, the byproduct polyethylene wax, and the Fischer-Thropsch wax. For example, they may include PetroliteRC-4040, PolywaxR1000, 2000 and 3000, a low molecular weight polyethylene wax available from Petrolite Corp.; EscomerRH-101, a modified polyethylene wax available from Exxon Chemical Co.; MarcusR100, 200 and 300, a low molecular weight byproduct polyethylene wax available from Marcu Chemical Co. that is a subsidiary of H.R.D. Corp. in Houston, Tex.; ParaflintRH-1, H-4 and H-8, a Fischer-Tropsch wax available from Sasol-SA/Moore & Munger in Shelton, Conn.; and PetroliteRPX-100, a Fischer-Tropsch wax available from Bareco. In addition, they may include a polypropylene wax, an ethylene vinyl acetate wax, an oxidized polyethylene wax, an ethylene acrylate wax and other wax, which are available from Hoechst Celanese and Eastman Chemical, but are not particularly limited thereto. A content of the wax may be contained, for example, in an amount of 0% by weight to 40% by weight, for example, 15% by weight to 35% by weight, for example, 20% by weight to 30% by weight, based on the weight of the hot melt adhesive composition, but it can be appropriately adjusted by those skilled in the art.

According to an embodiment, the tackifying resin may be contained to impart tack to the hot melt adhesive composition. The tackifying resin may include various types of hydrocarbon-based compositions that are useful and may include, for example, aliphatic C5 resin, polyterpene resin, hydrogenated resin, mixed aliphatic-aromatic resin, rosin ester, and hydrogenated rosin ester. Specifically, the tackifying resin may include, for example, aliphatic, cyclic aliphatic and aromatic hydrocarbon and modified hydrocarbon and hydride; terpene and modified terpene and hydride; rosin and rosin derivative and hydride; and a mixture thereof. The tackifying resin has a softening point of 70° C. to 150° C. by a circulating method, and are generally measured using a Brookfield viscometer and have a viscosity of 2000 centipoise (20 g/(cm sec)) or less at 350° F. (177° C.). The tackifying resin with different degree of hydrogenation or saturation is also available. For example, it may include EastotacRH-100, H-115 and H-130 from Eastman Chemical in Kingsport, Tenn. The tackifying resin is partially hydrogenated cyclic aliphatic petroleum-based hydrocarbon resin having a softening point of 100° C., 115° C. and 130° C., respectively. The tackifying resin is available as E-grade, R-grade, L-grade and W-grade showing different degrees of hydrogenation, wherein E has the smallest hydrogenation and W has the largest hydrogenation. The E grade has a bromine value 15, the R grade has a bromine value 5, the L grade has a bromine value 3, and the W grade has a bromine value 1. EastotacRH-142 R from Eastman Chemical Co. has a softening point of about 140° C. The other types of the tackifying resin may include, for example, EscorezR5300 and 5400, partially hydrogenated cyclic aliphatic petroleum-based hydrocarbon resins, and EscorezR5600, a partially hydrogenated aromatic modified petroleum-based hydrocarbon resin, both of which are available from Exxon Chemical Co. in Houston, Tex.; WingtackRExtra, an aliphatic, aromatic petroleum-based hydrocarbon resin available from Goodyear Chemical Co. in Akron, Ohio; HercoliteR2100, a partially hydrogenated cyclic aliphatic petroleum-based hydrocarbon resin available from Hercules Inc. in Wilmington, Del.; and ZonatacR 105 and 501 Lite, a styrenated terpene resin made from d-limonene and available from Arizona Chemical Co. in Panama City, Fla. A commercially available product with other hydrogenation grade may include SylvatacR1103, a pentaerythritol rosin ester available from Arizona Chemical Co.; UnitacRR-100 Lite, a pentaerythritol rosin ester from Union Camp in NJ, Wayne; PermalynR305, an erythritol-modified wood rosin available from Hercules, and Foral 105, a highly hydrogenated pentaerythritol rosin ester available from Hercules; SylvatacRE-85 and 295, rosin acids of melting point 85° C. and 95° C. available from Arizona Chemical Co.; and ForalAX, a hydrogenated rosin acid of melting point 70° C. available from Hercules Inc. Nirez V-2040 is a phenolic modified terpene resin available from Arizona Chemical Co. Further, the other tackifying resin may include a α-methylstyrene resin and a hydrogenated hydrocarbon resin which may contain an aliphatic or aromatic hydrocarbon, for example, types of these resins available from Hercules, Inc.

Examples of the aliphatic resin may include those available under the trade names Escorez™, Piccotac™, Mercures™, Wingtack™, Hi-Rez™, Quintone™, Tackirol™, and the like. Examples of the polyterpene resin may include those available under the trade names Nirez™, Piccolyte™, Wingtack™, Zonarez™, and the like. Examples of the hydrogenated resin may include those available under the trade names Escorez™, Arkon™, Clearon™, and the like. Examples of the mixed aliphatic-aromatic resin may include those available under the trade names Escorez™, Regalite™, Hercures™, AR™, Imprez™, Norsolene™ M.Marukarez™, Arkon™, M.Quintone™, and the like. The other tackifiers may be used as long as they are compatible with homogeneous or substantially linear ethylene/α-olefin interpolymers and waxes.

In some embodiments, the hot melt adhesive composition may be prepared without using the tackifying resin or with a small amount of the tackifier. Since the tackifier is generally decomposed at a high temperatures, the hot melt adhesives that minimize the use of the tackifier can exhibit an improved thermal stability. The content of the tackifying resin may be contained, for example, in 20% by weight or less, for example, 15% by weight or less, for example, 10% by weight or less. As another example, the hot melt adhesive of the present invention suitable for using at a low application temperature may contain the tackifying resin of the present invention, for example, in an amount of 10% by weight to 60% by weight, for example, 20% by weight to 55% by weight, for example, 25% by weight to 50% by weight, for example, 30% by weight to 45% by weight, based on the total weight of the hot melt adhesive composition.

As the present invention allows for various changes and numerous embodiments, particular embodiments will be illustrated in the drawings and specifically explained in the detailed description. However, this is not intended to limit the present invention to the specific embodiments, and it should be understood to embrace all modifications, equivalents, and substitutes included in the spirit and scope of the present invention.

Suitable Host Strains

In some embodiments, the host strain is *E. coli* K-12 strain LS5218 (Sprat et al., J. Bacteriol. 146 (3):1166-1169 (1981); Jenkins and Nunn, J. Bacteriol. 169 (1):42-52 (1987)) or strain MG1655 (Guyer et al., Cold Spr. Harb. Symp. Quant. Biol. 45:135-140 (1981)). Other suitable *E. coli* K-12 host strains include, but are not limited to, WG1 and W3110 (Bachmann Bacteriol. Rev. 36(4):525-57 (1972)). Alternatively, *E. coli* strain W (Archer et al., BMC Genomics 2011, 12:9 doi:10.1186/1471-2164-12-9) or *E. coli* strain B (Delbruck and Luria, Arch. Biochem. 1:111-141 (1946)) and their derivatives such as REL606 (Lenski et al., Am. Nat. 138:1315-1341 (1991)) are other suitable *E. coli* host strains.

Other exemplary microbial host strains include but are not limited to: *Ralstonia eutropha, Zoogloea ramigera, Allochromatium vinosum, Rhodococcus ruber, Delftia acidovorans, Aeromonas caviae, Synechocystis* sp. PCC 6803, *Synechococcus elongatus* PCC 7942, *Thiocapsa pfenigii, Bacillus megaterium, Acinetobacter baumannii, Acinetobacter baylyi, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor*, and *Clostridium acetobutylicum*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

Exemplary algal strains include but are not limited to: *Chlorella* strains, species selected from: *Chlorella minutissima, Chlorella emersonii, Chlorella sorokiniana, Chlorella ellipsoidea, Chlorella* sp., or *Chlorella* protothecoides.

Production of Transgenic Host for Producing 4HB Transgenic (recombinant) hosts for producing PHB-co-4HB are genetically engineered using conventional techniques known in the art. The genes cloned and/or assessed for host strains producing PHB-co-4HB are presented below in Table 1, along with the appropriate Enzyme Commission number (EC number) and references. Some genes were synthesized for codon optimization while others were cloned via PCR from the genomic DNA of the native or wild-type host. As used herein, "heterologous" means from another host. The host can be the same or different species.

TABLE 1

| Gene name | Enzyme name | EC number | Accession No. or Reference |
|---|---|---|---|
| phaA5 | Acetyl-CoA acetyltransferase (a.k.a. beta-ketothiolase) | 2.3.1.9 | 2VU2_A |
| phaB5 | Acetoacetyl-CoA reductase | 1.1.1.36 | P23238 |
| sucD* | Succinate semialdehyde dehydrogenase | 1.2.1.76 | Gene/Protein ID 1; U.S. patent application No. 2011/024612 |
| ssaR$_{At}$* | Succinic semialdehyde reductase | 1.1.1.61 | Gene/Protein ID 2; U.S. patent application No. 2011/024612 |
| orfZ | CoA transferase | 2.8.3.n | AAA92344 |
| phaC3/C5 | Polyhydroxyalkanoate synthase | 2.3.1.n | Gene/Protein fusion protein ID 4; U.S. Pat. No. 6,316,262; U.S. patent application No. 20100168481 A1 |
| yneI | Succinate-semialdehyde dehydrogenase, NAD+-dependent | 1.2.1.24 | NP_416042 |
| gabD | Succinate-semialdehyde dehydrogenase, NADP+- dependent | 1.2.1.16 | NP_417147 |
| astD | Aldehyde dehydrogenase | 1.2.1.71 | NP_416260 |
| tesA | Multifunctional acyl-CoA thioesterase I and protease I and lysophospholipase L1 | 3.1.1.5 3.1.2.14 | NP_415027 |
| tesB | Thioesterase II | 3.1.2.20 | ZP_08342109 |
| yciA | Acyl-CoA thioesterase | 3.1.2.20 | NP_415769 |

Suitable Extrachromosomal Vectors and Plasmids

A "vector," as used herein, is an extrachromosomal replicon, such as a plasmid, phage, or cosmid, into which another DNA segment may be inserted so as to bring about the replication of the inserted segment. Vectors vary in copy number, depending on their origin of replication, and size. Vectors with different origins of replication can be propagated in the same microbial cell unless they are closely related such as pMB1 and ColE1. Suitable vectors to express recombinant proteins can constitute pUC vectors with a pMB1 origin of replication having 500-700 copies per cell, pBluescript vectors with a ColE1 origin of replication having 300-500 copies per cell, pBR322 and derivatives with a pMB1 origin of replication having 15-20 copies per cell, pACYC and derivatives with a p15A origin of replication having 10-12 copies per cell, and pSC101 and derivatives with a pSC101 origin of replication having about 5 copies per cell as described in the QIAGEN® Plasmid Purification Handbook (found on the world wide web at: //kirshner.med-.harvard.edu/files/protocols/QIAGEN_QIAGENPlasmid-Purification_EN.pdf).

A widely used vector is pSE380 that allows recombinant gene expression from an IPTG-inducible trc promoter (Invitrogen, La Jolla, Calif.).

Example 1

Preparation of PHB-Co-4HB with 4HB Content of 90%

Production of PHB-Co-4HB with 4HB Co-Monomer Content of 90% from Glucose as Sole Carbon Source This example shows preparation of PHB-co-4HB with 4HB co-monomer content of 90% from glucose as sole carbon source in an engineered E. coli host strain. The strain was constructed using the well-known biotechnology tools and methods described above. It contained chromosomal deletions of yneI, gabD, tesB, tesA, yciA, and astD. (See U.S. Pat. No. 10,323,261B2)

Strain 1 used in Example 1.
Strain Operon Configuration
$P_x$-phaC3/C5-$T_{trpL}$-$P_{uspA}$-sucD*-ssaR$_{At}$*, $P_{uspA}$-phaA5-phaB5, $P_{rpsU}$-orfZ The production medium consisted of 1×E2 minimal salts, 5 mM MgSO$_4$, and 1×Trace Salts Solution. The initial carbon source consisted of 20-30 g/L glucose 50×E2 stock solution consists of 1.28 M NaNH$_4$HPO$_4$.4H$_2$O, 1.64 M K$_2$HPO$_4$, and 1.36 M KH$_2$PO$_4$.1000×Trace Salts Solution is prepared by adding per 1 L of 1.5 N HCl: 50 g FeSO$_4$.7H$_2$O, 11 g ZnSO$_4$.7H$_2$O, 2.5 g MnSO$_4$.4H$_2$O, 5 g CuSO$_4$.5H$_2$O, 0.5 g (NH$_4$)$_6$Mo$_7$O$_{24}$.4H$_2$O, 0.1 g Na$_2$B$_4$O$_7$, and 10 g CaCl$_2$.2H$_2$O.

To produce PHB-co-4HB with 4HB co-monomer content of 90%, the strain was cultured in 250 mL baffled flask containing 50 mL of LB and appropriate antibiotics at 37° C. with shaking at 250 rpm. When the OD at 600 nm of the culture broth reached 1, 6 to 12 ml of the culture broth was transferred to 20 L fermentor containing 5400 mL of the production medium. The cells in the fermentor cultured 37° C. with agitation at 250-800 rpm and aeration 1 vvm until the OD at 600 nm reached 10-12. Then the temperature was dropped over 1-3 hours period from 37 to 27-30° C. pH was kept between 6.0 and 7.0 with sodium hydroxide or other non-ammonia base. In order to limit biomass production and promote PHB-co-4HB production, ammonia-limited condition was maintained by pulse-feed ammonia. Airflow and back pressure were kept constant at 1.0-2.0 vvm and 4-10 psig, respectively. Agitation was adjusted between 250-800 rpm to keep dissolved oxygen above 10% of air saturation. Glucose was fed continuously to culture in order to keep glucose in excess at 5-10 g/L. The culture was harvested 35 hours after temperature drop.

Thereafter, culture was analyzed for polymer content. At the end of the experiment, culture was spun down at 4150 rpm, washed once with distilled water, frozen at −80° C. for at least 30 minutes, and lyophilized overnight. The next day, a measured amount of lyophilized cell pellet was added to a glass tube, followed by 3 mL of butanolysis reagent that consists of an equal volume mixture of 99.9% n-butanol and 4.0 N HCl in dioxane with 2 mg/mL diphenylmethane as internal standard. After capping the tubes, they were vortexed briefly and placed on a heat block set to 93° C. for six hours with periodic vortexing. Afterwards, the tube was cooled down to room temperature before adding 3 mL distilled water. The tube was vortexed for approximately 10 s before spinning down at 620 rpm (Sorvall Legend RT benchtop centrifuge) for 2 min. 1 mL of the organic phase was pipetted into a GC vial, which was then analyzed by gas chromatography-flame ionization detection (GC-FID) (Hewlett-Packard 5890 Series II). The quantity of PHA in the cell pellet was determined by comparing against standard curves for both 3HB and 4HB (for PHB-co-4HB analysis). The 4HB standard curve was generated by adding different amounts of a 10% solution of γ-butyrolactone (GBL) in butanol to separate butanolysis reactions. The 3HB standard curve was generated by adding different amounts of 99% ethyl 3-hydroxybutyrate to separate butanolysis reactions.

Comparative Example 1

Preparation of PHB-Co-4HB with 4HB Content of 10%
PHB-co 4HB with 4HB co-monomer content of 10% was prepared as described in Example 1 except using the Strain 12 and back pressure was not applied to keep dissolved oxygen between 0 to 10% of air saturation after the temperature drop.
Strain 12
Strain Operon Configuration $P_x$-phaC3/C5-$T_{trpL}$-$P_{uspA}$-phaA5-phaB5-$T_{1006}$-sucD*-ssaR$_{At}$*, $P_{rpsU}$-orfZ Comparative Example 2

Preparation of PHB-Co-4HB with 4HB Content of 50%
PHB-co 4HB with 4HB co-monomer content of 50% was prepared as described in Example 1 except back pressure was not applied to keep dissolved oxygen between 0 to 10% of air saturation after the temperature drop.
Purification Process:
The fermented broth in water was treated in centrifuge to remove water followed by addition of deionized water three times (200 mL×3) to get rid of lyophilized cell and substrates then chloroform was added to the crude wet polymer solution till all solid material was dissolved completely. The resulting solution was poured into large amount of ethanol to precipitate as the white powder. In order to measure both mechanical properties evaluation experiments and thermal properties, remaining wet polymer was allowed to stand until it appeared to be dry (water quantity was around 2500 ppm)

Experimental Example 2: Content of Biobase of PHB-Co-4HB Copolymer

The copolymer purified from strain 1 as described above was used to determine the biobased content by radiocarbon dating based on ASTM D6866 by Beta Analytic (Miami, Fla., USA). The purified copolymer from strain 1 was determined to contain a biobased content of 97%.

Experimental Example 3: Acid Value Analysis

Total Acid Number (TAN) is measured with 888 Titrando of METROHM. The experimental procedure determines the sum of all acid compounds present in samples by an acid-base titration using potassium hydroxide (KOH) as titrant. TAN is expressed in mg of KOH per g of sample.
As the polyhydroxyalkanoate copolymer molecules are non-aqueous, they are diluted in chloroform. To prepare the sample, A sample is dissolved into chloroform about the concentration (0.1 g/ml) approximately.
The solvent for KOH is methanol (0.1 N potassium hydroxide in methanol). The TAN which mainly an indication of the degree of oxidation and hydrolysis, is expressed as the mass of KOH in milligrams that is required to neutralize the acids in 1 g of sample. Furthermore, the TAN measures acidic constituents using a potentiometer to determine the last equivalence point (EP). The potentiometer output is monitored, while KOH is titrated into the solution.

TAN (mg of KOH/g)=$(EPn-C31)\times C01\times C03/C00$ where EPn is the consumption of KOH at the final equivalent point (mL), C00 is the weight of the sample (g), C01 is 0.1 (concentration of the titrant, mol/L), C03 is 56.106 [M (KOH) in g/mol], and C31 is the consumption in zero titration (mL).
As a result, it was confirmed that an acid value of the composition according to Example 1 having 4HB of 90% was 1.18 mg/g.

Experimental Example 4: Analysis of Color Difference and Refractive Index

Color difference b* APHA is a measurement index indicating yellowness, measured using a CM-5 Spectrophotom-

TABLE 1

Results of Representative PHAs upon Changing 4HB(%)

|  | | | Thermal Properties | | | | TAN | |
| --- | --- | --- | --- | --- | --- | --- | --- | --- |
|  | Mw(*10$^3$) | 4HB(%) | Tg(° C.) | Tm(° C.) | Tc(° C.) | Td(° C.) | b* | (mg/g) | RI |
| Comparative Example 1 | 445 | 10 | −4.5 | 150 | 70 | 285 | 7.8 | 5.65 | 1.45 |
| Comparative Example 2 | 520 | 50 | −30 | 148 | 103 | 281 | 17.5 | 4.98 | 1.48 |
| Example 1 | 400 | 90 | x | 40 | x | 279 | 11.0 | 1.18 | 1.42 |

Experimental Example 1: Measurement of Glass Transition Temperature

The copolymers were used to determine the PHA composition. The glass transition temperature (Tg) was measured using differential scanning calorimetry (DSC) analysis. Table 1 lists the 4HB content and the Tg measured from the copolymers. The glass transition temperature decreased with higher 4HB content in the copolymer.

eter manufactured by Konica Minolta. Before the measurement, zero calibration was set up using a white calibration sheet provided by the manufacturer, and was prepared by setting it to Specular Component Included (SCI) mode. The sample to be measured was filled into a petri dish having a diameter of 30 mm, and the sample was measured 5 times to discard two measurement values with large deviation and take the remaining three average values. A refractive index was also measured using the product manufactured by Konica Minolta in accordance with the above method. As a result, it was confirmed that the color difference of the composition according to Example 1 was 11.0 b* (APHA), and the refractive index (RI) thereof was 1.42.

Experimental Example 5: Measurement of Melting Point, Decomposition Temperature, Melt Flow Index, and Molecular Weight Thermogravimetric analysis (TGA) of solid polymer samples was performed using TGA 2950 from TA Instruments (New Castle, Del.) at the heating rate of 10° C. min-1 in a nitrogen atmosphere. Solid-state differential calorimetry (DSC) experiments were performed with DSC 2920 from TA Instruments (New Castle, Del.) at the heating rate 10° C. $min^{-1}$ in a nitrogen atmosphere.

Differential Scanning Calorimetry (DSC) experiments were performed on a DSC 450 from TA Instruments, baselines were subtracted to obtain the excess heat capacity curves, which were analyzed using the manufacturer supplied MicroCal Origin DSC software, Version 5.0.

GPC analyses of polymers were performed with Agilent 1100 chromatograph equipped with two PLgel 5 μm MIXED-C and one PLgel 5 μm 1000 Å columns connected in series, using chloroform as a mobile phase, and calibrated against polystyrene internal standards (Mw 300~2,000,000).

As a result, it was confirmed that a melting point (Tm) of the composition according to Example 1 was 40° C., a decomposition temperature (Td) thereof was 279° C., a melt flow index (MFI) thereof was 5 to 6 g/10 min, a molecular weight thereof was 400 Mw ($10^3$), and PDI was 2.25.

Experimental Example 6: Analysis of Elongation and Tensile Strength

Figure 1:
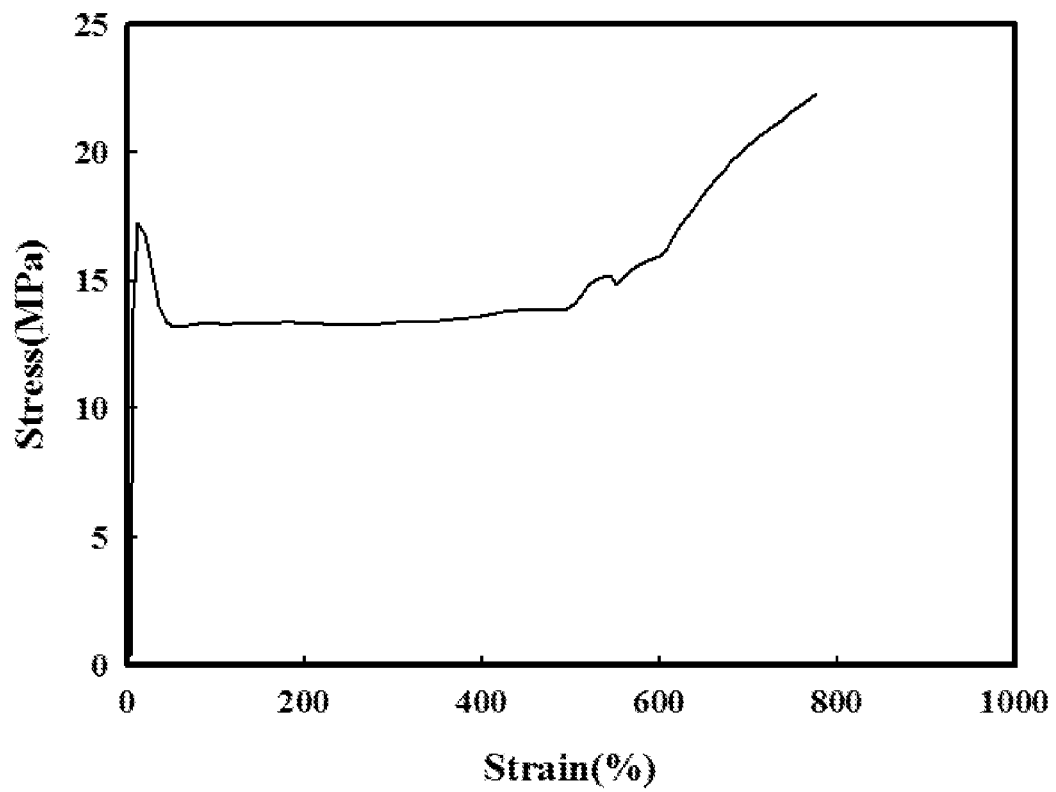
FIG. 1 is a graph showing a stress of a sample against a strain of PHA having a content of 4-hydroxy butyrate (4HB) unit of 10% according to the present invention.

The 4HB contents of PHA used in Example and Comparative Examples were 10% (Comparative Example 1), 50% (Comparative Example 2), and 90% (Example 1), and the weight average molecular weight was found to be 440 to 550 KDa. Mechanical properties were evaluated using these polymers. A resin of 10 phr (part) was added to chloroform or methyl-isobutyl ketone (MIBK) having a value similar to the solubility parameter value of PHA and was stirred at 60° C. for at least 3 hr to completely dissolve it. Thereafter, the solution was coated on a PET release film using a Dr. blade spin coater and dried at a room temperature for 24 hours to produce a film having a thickness of about 200 um. The fabricated sample was measured for the mechanical properties of a tensile strength and an elongation at break using a universal tensile tester (UTM) device of LR30K model manufactured by Lloyd according to the ASTM-D882 standard. A specimen having a width of 10 mm and a length of 50 mm was prepared using a load cell of 500 N, and measured for the tensile strength and the elongation at break at a speed of 200 mm/min with a gage length of 30 mm. In this manner, the same film was measured 7 times or more to discard the two measurement values having the most deviation and to take the average value of the rest. As a result, it was confirmed that the elongation of the composition according to Example 1 was 1,700 to 1,900%, and the tensile strength was 5 to 8 MPa. Further, the graphs showing stresses of the samples against strains were shown in FIGS. 1 to 3. FIG. 1 relates to Comparative Example 1 (4HB content of 10%), FIG. 2 relates to Comparative Example 2 (4HB content of 50%), and FIG. 3 relates to Example 1 (4HB content of 90%). As shown in FIGS. 1 to 3, the physical properties were confirmed to vary with the content of the 4HB. Since the change in these physical properties is not proportional to the content of the 4HB monomer, it can be seen that the change in the 4HB content and the physical properties is not predictable.

Although the Examples of the present invention have been described above, the present invention can be prepared in various forms with each other without being limited to the above Examples. Any person who has an ordinary knowledge in the technical field to which the present invention pertains will appreciate that the invention can be implemented in other specific forms without changing the technical spirit or essential features of the present invention. Therefore, it should be understood that the Examples described above are illustrative in all respects and are not restrictive.

The following sequence listings are also being submitted in a .txt file entitled "5107.55US01_SEQUENCE_ST25.txt," which is incorporated herein by reference.

```
Sequence List
Gene ID 001 Nucleotide Sequence:
Clostridium kluyyeri succinate
semialdehyde dehydrogenase gene sucD*
ATGTCCAACGAGGTTAGCATTAAGGAGCTGATTGAGAAGGCGAAAGTGGC

GCAGAAAAAGCTGGAAGCGTATA

GCCAAGAGCAAGTTGACGTTCTGGTCAAGGCGCTGGGTAAAGTTGTGTAC

GACAACGCCGAGATGTTCGCGAA

AGAGGCGGTGGAGGAAACCGAGATGGGTGTTTACGAGGATAAAGTGGCTA

AATGTCATCTGAAATCTGGTGCA

ATCTGGAATCACATTAAAGATAAGAAACCGTTGGTATTATCAAGGAAGA

ACCGGAGCGTGCGCTGGTGTACG

TCGCGAAGCCTAAAGGTGTTGTGGCGGCGACGACCCCTATCACCAATCCT

GTGGTTACCCCGATGTGTAACGC

GATGGCAGCAATTAAAGGTCGCAACACCATCATTGTCGCCCCCGCATCCG

AAGGCGAAGAAGGTGAGCGCGCA

CACCGTGGAGCTGATGAATGCAGAACTGAAAAAGTTGGGTGCGCCGGAAA

ACATTATCCAGATCGTTGAAGCC

CCAAGCCGTGAAGCAGCCAAGGAGTTGATGGAGAGCGCAGACGTGGTTAT

CGCCACGGGTGGCGCAGGCCGTG

TTAAAGCAGCGTACTCCTCCGGCCGTCCGGCATACGGTGTCGGTCCGGGC

AATTCTCAGGTCATTGTCGATAA

GGGTTACGATTATAACAAAGCTGCCCAGGACATCATTACCGGCCGCAAGT

ATGACAACGGTATCATTTGCAGC

TCTGAGCAGAGCGTGATCGCACCGGCGGAGGACTACGACAAGGTCATCGC

GGCTTTCGTCGAGAATGGCGCGT

TCTATGTCGAGGATGAGGAAACTGTGGAGAAATTCCGTAGCACGCTGTTC

AAGGATGGCAAGATCAATAGCAA

AATCATCGGTAAATCCGTGCAGATCATCGCTGACCTGGCTGGTGTCAAGG

TGCCGGAAGGCACCAAGGTGATC

GTGTTGAAGGGCAAGGGTGCCGGTGAAAAGGACGTTCTGTGCAAGGAGAA
```

AATGTGCCCGGTCCTGGTTGCCC

TGAAATATGACACCTTTGAGGAGGCGGTCGAGATCGCGATGGCCAACTAT

ATGTACGAGGGTGCGGGCCATAC

CGCCGGTATCCACAGCGATAACGACGAGAATATCCGCTACGCGGGTACGG

TGCTGCCAATCAGCCGTCTGGTT

GTCAACCAGCCAGCAACTACGGCCGGTGGTAGCTTTAACAATGGTTTTAA

TCCGACCACCACCTTGGGCTGCG

GTAGCTGGGGCCGTAACTCCATTAGCGAGAACCTGACGTATGAGCATCTG

ATTAATGTCAGCCGTATTGGCTA

TTTCAATAAGGAGGCAAAAGTTCCTAGCTACGAGGAGATCTGGGGTTAA

Gene ID 001 Amino Acid Sequence: Clostridium
kluyveri succinate semialdehyde dehydrogenase
gene SucD*
MSNEVSIKELIEKAKVAQKKLEAYSQEQVDVLVKALGKVVYDNAEMFAKE

AVEETEMGVYEDKVAKCHLKSGA

IWNHIKDKKTVGIIKEEPERALVYVAKPKGVVAATTPITNPVVTPMCNAM

AAIKGRNTIIVAPHPKAKKVSAH

TVELMNAELKKLGAPENIIQIVEAPSREAAKELMESADVVIATGGAGRVK

AAYSSGRPAYGVGPGNSQVIVDK

GYDYNKAAQDIITGRKYDNGIICSSEQSVIAPAEDYDKVIAAFVENGAFY

VEDEETVEKERSTLEKDGKINSK

IIGKSVQIIADLAGVKPEGTKVIVLKGKGAGEKDVLCKEKMCPVLVALK

YDTELEAVEIAMANYMYEGAGHT

AGIHSDNDENIRYAGTVLPISRLVVNQPATTAGGSENNGENPTTTLGCGS

WGRNSISENLTYEHLINVSRIGY

FNKEAKVPSYEEIWG

Gene ID 002 Nucleotide Sequence: Arabidopsis
thaliana succinic semialdehyde reductase
gene ssaRAt*
ATGGAAGTAGGTTTTCTGGGTCTGGGCATTATGGGTAAAGCTATGTCCAT

GAACCTGCTGAAAAACGGTTTCA

AAGTTACCGTGTGGAACCGCACTCTGTCTAAATGTGATGAACTGGTTGAA

CACGGTGCAAGCGTGTGCGAGTC

TCCGGCTGAGGTGATCAAGAAATGCAAATACACGATCGCGATGCTGAGCG

ATCCGTGTGCAGCTCTGTCTGTT

GTTTTCGATAAAGGCGGTGTTCTGGAACAGATCTGCGAGGGTAAGGGCTA

CATCGACATGTCTACCGTCGACG

CGGAAACTAGCCTGAAAATTAACGAAGCGATCACGGGCAAAGGTGGCCGT

TTTGTAGAAGGTCCTGTTAGCGG

TTCCAAAAAGCCGGCAGAAGACGGCCAGCTGATCATCCTGGCAGCAGGCG

ACAAAGCACTGTTCGAGGAATCC

ATCCCGGCCTTTGATGTACTGGGCAAACGTTCCTTTTATCTGGGTCAGGT

GGGTAACGGTGCGAAAATGAAAC

TGATTGTTAACATGATCATGGGTTCTATGATGAACGCGTTTAGCGAAGGT

CTGGTACTGGCAGATAAAAGCGG

TCTGTCTAGCGACACGCTGCTGGATATTCTGGATCTGGGTGCTATGACGA

ATCCGATGTTCAAAGGCAAAGGT

CCGTCCATGACTAAATCCAGCTACCCACCGGCTTTCCCGCTGAAACACCA

GCAGAAAGACATGCGTCTGGCTC

TGGCTCTGGGCGACGAAAACGCTGTTAGCATGCCGGTCGCTGCGGCTGCG

AACGAAGCCTTCAAGAAAGCCCG

TAGCCTGGGCCTGGGCGATCTGGACTTTTCTGCTGTTATCGAAGCGGTAA

AATTCTCTCGTGAATAA

Gene ID 002 Amino Acid Sequence: Arabidopsis
thaliana succinic semialdehyde reductase
gene S saRAt*
MEVGFLGLGIMGKAMSMNLLKNGFKVTVWNRTLSKCDELVEHGASVCESP

AEVIKKCKYTIAMLSDPCAALSV

VEDKGGVLEQICEGKGYIDMSTVDAETSLKINEAITGKGGREVEGPVSGS

KKPAEDGQLIILAAGDKALFEES

IPAFDVLGKRSFYLGQVGNGAKMKLIVNMIMGSMMNAFSEGLVLADKSGL

SSDTLLDILDLGAMTNPMFKGKG

PSMTKSSYPPAFPLKHQQKDMRLALALGDENAVSMPVAAAANEAFKKARS

LGLGDLDFSAVIEAVKFSRE

Gene ID 004 Nucleotide Sequence: Pseudomonas
putida/Zoogloea ramigera polyhydroxyalkanoate
synthase fusion gene phaC3/C5
ATGAGTAACAAGAACAACGATGAGCTGCAGTGGCAATCCTGGTTCAGCAA

GGCGCCCACCACCGAGGCGAACC

CGATGGCCACCATGTTGCAGGATATCGGCGTTGCGCTCAAACCGGAAGCG

ATGGAGCAGCTGAAAAACGATTA

TCTGCGTGACTTCACCGCGTTGTGGCAGGATTTTTTGGCTGGCAAGGCGC

CAGCCGTCAGCGACCGCCGCTTC

AGCTCGGCAGCCTGGCAGGGCAATCCGATGTCGGCCTTCAATGCCGCATC

TTACCTGCTCAACGCCAAATTCC

TCAGTGCCATGGTGGAGGCGGTGGACACCGCACCCCAGCAAAAGCAGAAA

ATACGCTTTGCCGTGCAGCAGGT

GATTGATGCCATGTCGCCCGCGAACTTCCTCGCCACCAACCCGGAAGCGC

AGCAAAAACTGATTGAAACCAAG

GGCGAGAGCCTGACGCGTGGCCTGGTCAATATGCTGGGCGATATCAACAA

GGGCCATATCTCGCTGTCGGACG

AATCGGCCTTTGAAGTGGGCCGCAACCTGGCCATTACCCCGGGCACCGTG

ATTTACGAAAATCCGCTGTTCCA

GCTGATCCAGTACACGCCGACCACGCCGACGGTCAGCCAGCGCCCGCTGT

TGATGGTGCCGCCGTGCATCAAC

AAGTTCTACATCCTCGACCTGCAACCGGAAAATTCGCTGGTGCGCTACGC

GGTGGAGCAGGGCAACACCGTGT

TCCTGATCTCGTGGAGCAATCCGGACAAGTCGCTGGCCGGCACCACCTGG
GACGACTACGTGGAGCAGGGCGT

GATCGAAGCGATCCGCATCGTCCAGGACGTCAGCGGCCAGGACAAGCTGA
ACATGTTCGGCTTCTGCGTGGGC

GGCACCATCGTTGCCACCGCACTGGCGGTACTGGCGGCGCGTGGCCAGCA
CCCGGCGGCCAGCCTGACCCTGC

TGACCACCTTCCTCGACTTCAGCGACACCGGCGTGCTCGACGTCTTCGTC
GATGAAACCCAGGTCGCGCTGCG

TGAACAGCAATTGCGCGATGGCGGCCTGATGCCGGGCCGTGACCTGGCCT
CGACCTTCTCGAGCCTGCGTCCG

AACGACCTGGTATGGAACTATGTGCAGTCGAACTACCTCAAAGGCAATGA
GCCGGCGGCGTTTGACCTGCTGT

TCTGGAATTCGGACAGCACCAATTTGCCGGGCCCGATGTTCTGCTGGTAC
CTGCGCAACACCTACCTGGAAAA

CAGCCTGAAAGTGCCGGGCAAGCTGACGGTGGCCGGCGAAAAGATCGACC
TCGGCCTGATCGACGCCCCGGCC

TTCATCTACGGTTCGCGCGAAGACCACATCGTGCCGTGGATGTCGGCGTA
CGGTTCGCTCGACATCCTCAACC

AGGGCAAGCCGGGCGCCAACCGCTTCGTGCTGGGCGCGTCCGGCCATATC
GCCGGCGTGATCAACTCGGTGGC

CAAGAACAAGCGCAGCTACTGGATCAACGACGGTGGCGCCGCCGATGCCC
AGGCCTGGTTCGATGGCGCGCAG

GAAGTGCCGGGCAGCTGGTGGCCGCAATGGGCCGGGTTCCTGACCCAGCA
TGGCGGCAAGAAGGTCAAGCCCA

AGGCCAAGCCCGGCAACGCCCGCTACACCGCGATCGAGGCGGCGCCCGGC
CGTTACGTCAAAGCCAAGGGCTG

A

Gene ID 004 Amino Acid Sequence: Pseudomonas
putiza/Zoogloea ramigera polyhydroxyalkano ate
synthase fusion gene PhaC3/C5
MSNKNNDELQWQSWFSKAPTTEANPMATMLQDIGVALKPEAMEQLKNDYL
RDFTALWQDFLAGKAPAVSDRRF

SSAAWQGNPMSAFNAASYLLNAKFLSAMVEAVDTAPQQKQKIRFAVQQVI
DAMSPANFLATNPEAQQKLIETK

GESLTRGLVNMLGDINKGHISLSDESAFEVGRNLAITPGTVIYENPLFQL
IQYTPTTPTVSQRPLLMVPPCIN

KFYILDLQPENSLVRYAVEQGNTVFLISWSNPDKSLAGTTWDDYVEQGVI
EAIRIVQDVSGQDKLNMFGFCVG

GTIVATALAVLAARGQHPAASLTLLTTFLDFSDTGVLDVFVDETQVALRE
QQLRDGGLMPGRDLASTFSSLRP

NDLVWNYVQSNYLKGNEPAAFDLLFWNSDSTNLPGPMFCWYLRNTYLENS
LKVPGKLTVAGEKIDLGLIDAPA

FIYGSREDHIVPWMSAYGSLDILNQGKPGANRFVLGASGHIAGVINSVAK
NKRSYWINDGGAADAQAWFDGAQ

EVPGSWWPQWAGFLTQHGGKKVKPKAKPGNARYTAIEAAPGRYVKAKG

---

What is claimed is:

1. A low-temperature processable aliphatic polyester comprising 3-hydroxybutyrate monomers and 4-hydroxybutyrate monomers as polyhydroxyalkanoate copolymer molecules,
wherein a content of the 4-hydroxybutyrate monomers is 76 to 98 mol %.

2. The low-temperature processable aliphatic polyester according to claim 1,
wherein a weight average molecular weight of the copolymer molecules is 200 to 800 kDa.

3. The low-temperature processable aliphatic polyester according to claim 1,
wherein the content of the 4-hydroxybutyrate monomers is 85 to 95 mol %.

4. The low-temperature processable aliphatic polyester according to claim 1,
having a melting point (Tm) of 30° C. to 100° C. and a decomposition temperature (Td) of 200° C. to 400° C.

5. The low-temperature processable aliphatic polyester according to claim 1,
having an acid value of 0.5 to 4.

6. The low-temperature processable aliphatic polyester according to claim 1,
having a color difference of b* of 1 to 15.

7. The low-temperature processable aliphatic polyester according to claim 1,
having a melt flow index (MFI) of 3 to 10.

8. The low-temperature processable aliphatic polyester according to claim 1,
having an elongation of 1000% to 2500%.

9. The low-temperature processable aliphatic polyester according to claim 1,
having a tensile strength of 1 MPa to 20 MPa.

10. The low-temperature processable aliphatic polyester according to claim 1,
having a refractive index ($nD^{25}$) of 1.3 to 1.7.

11. A method for preparing a low-temperature processable aliphatic polyester comprising 3-hydroxybutyrate monomers and 4-hydroxybutyrate monomers as polyhydroxyalkanoate copolymer molecules, wherein a content of the 4-hydroxybutyrate monomers is 76 to 98 mol %,
the method comprising the step of: culturing an organism in the presence of one or more carbon raw materials under conditions under which (a) the one or more carbon raw materials are converted to 3-hydroxybutyryl-CoA and 4-hydroxybutyryl-CoA and (b) the 3-hydroxybutyryl-CoA and the 4-hydroxybutyryl-CoA are polymerized to form the polyhydroxyalkanoate copolymer molecules, thereby forming the polyhydroxyalkanoate copolymer molecules.

12. The method for preparing the low-temperature processable aliphatic polyester according to claim 11,
wherein the organism has been genetically engineered to comprise enzymatic activities of a polyhydroxyalkanoate synthase, an acetyl-CoA acetyltransferase, an acetoacetyl-CoA reductase, a succinate semialdehyde dehydrogenase, a succinic semialdehyde reductase, and a CoA transferase by stable incorporation of genes encoding the polyhydroxyalkanoate synthase, the acetyl-CoA acetyltransferase, the acetoacetyl-CoA reductase, the succinate semialdehyde dehydrogenase, the succinic semialdehyde reductase, and the CoA transferase into the organism by introduction of one or more stable plasmids comprising the genes and/or by integration of the genes into the genome of the organism, and to not comprise enzymatic activities of either an NAD+-dependent succinate-semialdehyde dehydrogenase or an NADP+-dependent succinate-semialdehyde dehydrogenase or both.

13. The method for preparing the low-temperature processable aliphatic polyester according to claim 11,
wherein the one or more carbon raw materials, taken together, have a biobased content of ≥50%.

14. The method for preparing the low-temperature processable aliphatic polyester according to claim 11,
wherein the organism has further been genetically engineered (a) to comprise enzymatic activities of (i) an alpha-ketoglutarate decarboxylase or 2-oxoglutarate decarboxylase and (ii) an L-1,2-propanediol oxidoreductase, and (b) to not comprise enzymatic activities of one or more of (i) a thioesterase II, (ii) a multifunctional acyl-CoA thioesterase I and protease I and lysophospholipase L, (iii) an acyl-CoA thioesterase, and (iv) an aldehyde dehydrogenase.

15. The method for preparing the low-temperature processable aliphatic polyester according to claim 11,
wherein the one or more carbon raw materials comprise a carbon source selected from the group consisting of glucose, levoglucosan, sucrose, lactose, fructose, xylose, maltose, arabinose, and mixtures thereof.

16. The method for preparing the low-temperature processable aliphatic polyester according to claim 11,
wherein the one or more carbon raw materials comprise one or more of molasses, starch, a fatty acid, a vegetable oil, a lignocellulosic material, ethanol, acetic acid, glycerol, a biomass-derived synthesis gas, and methane originating from a landfill gas.

17. The method for preparing the low-temperature processable aliphatic polyester according to claim 11,
wherein the one or more carbon raw materials do not comprise γ-butyrolactone, 1,4-butanediol, 4-hydroxybutyrate, 3-hydroxybutyrate, α-ketoglutarate, oxaloacetate, malate, fumarate, citrate, succinate, or 3-hydroxybutyrate.

18. The method for preparing the low-temperature processable aliphatic polyester according to claim 11,
further comprising isolating the polyhydroxyalkanoate copolymer molecules from the organism, such that the polyhydroxyalkanoate copolymer composition is substantially free of the organism.

19. A low-temperature processable aliphatic polyester prepared by the method according to claim 11.

20. The low-temperature processable aliphatic polyester according to claim 19,
wherein the content of the 4-hydroxybutyrate monomers using the fermentation of a strain is 76 to 98 mol %.

21. An article comprising the low-temperature processable aliphatic polyester according to claim 1,
wherein the article is a biodegradable wax, a medical device, a low-temperature hot melt, a non-woven cloth, a bioplastic, a drug carrier, a medical wrap, a medical fiber, a medical filament, a medical stent, or an orthopedic prosthesis.

* * * * *